(12) United States Patent
Church (10) Patent No.: US 8,881,699 B2
(45) Date of Patent: Nov. 11, 2014

(54) FEED FORWARD DYNAMIC SPOOL VALVE (71) Applicant: Ford Global Technologies, LLC, Dearborn, MI (US)

(72) Inventor: Jeremy Walter Church, Belleville, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 21 days.

(21) Appl. No.: 13/762,018

(22) Filed: Feb. 7, 2013

(65) Prior Publication Data

US 2014/0216373 A1    Aug. 7, 2014

(51) Int. Cl.
F01L 1/34      (2006.01)
F01L 1/344     (2006.01)

(52) U.S. Cl.
CPC .................................. F01L 1/3442 (2013.01)
USPC .................... 123/90.17; 123/90.15

(58) Field of Classification Search
CPC . F01L 1/3442; F01L 1/34; F01L 2001/34433; F01L 2001/3443
USPC ................... 123/90.15, 90.17, 90.31
See application file for complete search history.

(56) References Cited

U.S. PATENT DOCUMENTS

| 5,803,031 | A  | * | 9/1998 | Moriya ................ 123/90.17 |
| 6,602,060 | B2 |   | 8/2003 | Zebuhr |
| 6,736,094 | B2 | * | 5/2004 | Ekdahl et al. ............ 123/90.15 |
| 8,079,332 | B2 |   | 12/2011 | Kim et al. |
| 8,145,404 | B2 |   | 3/2012 | Gauthier et al. |
| 2005/0028770 | A1 |   | 2/2005 | McCabe |
| 2005/0229687 | A1 |   | 10/2005 | McCabe et al. |
| 2010/0280739 | A1 |   | 11/2010 | Rollinger et al. |

FOREIGN PATENT DOCUMENTS

EP          1061038 A1     12/2000

* cited by examiner

*Primary Examiner* — Zelalem Eshete
(74) *Attorney, Agent, or Firm* — Julia Voutyras; Alleman Hall McCoy Russell & Tuttle LLP (57) ABSTRACT

A method of controlling a spool valve through feedback and feedforward mechanisms is described. In one example, a method includes actuating a spool valve via a solenoid to advance and retard a hydraulic variable cam timing actuator coupled to a camshaft, and while commanded to a null position to maintain current cam timing, modulating the solenoid with a component at a frequency synchronous to engine firing frequency to counteract cam torque oscillations. In this way, a spool valve may be maintained in a null position despite high cam torque oscillation frequency, thereby retaining oil in a solenoid assembly and improving can timing position.

20 Claims, 7 Drawing Sheets

FEED FORWARD DYNAMIC SPOOL VALVE

BACKGROUND/SUMMARY

Internal combustion engines may use variable cam timing (VCT) to improve fuel economy and emissions performance of a vehicle. One method of variable cam timing uses an Oil Pressure Actuated device, such as a vane type cam phaser. The phaser may be controlled by an electromechanically actuated spool valve that directs oil flow to one side or the other of the vane. The performance of this device is thus dependent on oil pressure, which can be a function of engine speed and leakage through various oil systems.

One example VCT system uses a spool valve with one inlet and two outlet flows. The spool valve thus has two functions—to let control oil in and to let drain oil out. The control oil inlet is typically used to control VCT position, often through feedback and/or feed forward methods.

The inventors herein have recognized that at high engine RPM, available control systems may be insufficient to accurately control VCT position during cam torque oscillation events while maintaining cam timing at a current cam timing. Significant amounts of oil may be unintentionally drained out of the system, necessitating additional control oil to be taken in during future control events. Additionally, when oil is forced out of the drain ports, the cam may move out of its desired position, or may oscillate to a greater degree. This may result in both undesired engine knocking and subsequent degradation to engine parts.

In one example, these issues may be addressed by a method, comprising actuating a spool valve via a solenoid to advance and retard a hydraulic variable cam timing actuator coupled to a camshaft; and, while commanded to a null position to maintain current cam timing, modulating the solenoid with a component at a frequency synchronous to engine firing frequency to counteract cam torque oscillations.

In another example these issues may be addressed by a system for an engine, comprising a hydraulically actuated variable cam timing actuator, a cam with oil passages used to deliver oil from oil passages in a cam cap to the variable cam timing actuator coupled to the cam, a hydraulic spool valve coupled to the variable cam timing actuator, the spool valve adjustable among a plurality of positions including a null position to maintain current cam timing, and a solenoid configured to control the position of the spool valve by modulating the spool valve in the null position with a component at a frequency synchronous to engine firing frequency to counteract cam torque oscillations.

In this way, it is possible to generate actuation of the spool valve to counteract the effects of the cam torque on the oil flow, so that the oil volume in the variable cam timing actuator is maintained and the cams better maintain the current cam timing. Specifically, while commanded to the null position to maintain current cam timing, for example based on feedback and/or feedforward control, the solenoid modulation enables the spool valve to block the flow of oil that may otherwise occur due to the force on the camshaft by the actuation of the cylinder valves. By blocking the unintended flow of oil into, or out of, the hydraulic variable cam timing actuator's advance and retard chambers, the hydraulic system is stiffened and the cams move away from the current timing to a lesser degree, thereby better maintaining the combustion performance consistency across the various cylinders of the engine. Such is possible even with time varying disturbance torques acting on the camshaft from the cylinder valve actuation. Further, by modulating at a frequency synchronous with combustion frequency, it is possible to better align the modulation to the actual kinematic torsion acting on the camshaft and thus counteract and cancel such effects.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED SPECIFICATION

The following description relates to systems and methods for controlling an engine of a vehicle, the engine having a variable cylinder valve system, such as a variable cam timing. For example, the engine may include a VCT phaser to adjust the cam timing, where the phaser is included in a hydraulic system. The engine may be configured to include a controller configured to control the activation signal for a solenoid that in turn controls the position of a spool valve positioned within the hydraulic system. In one example, the activation signal for the solenoid may be subject to feed forward modulation to maintain the position of the spool valve to block oil from draining out of the hydraulic system, thereby improving performance of the VCT system.

Figure 1:
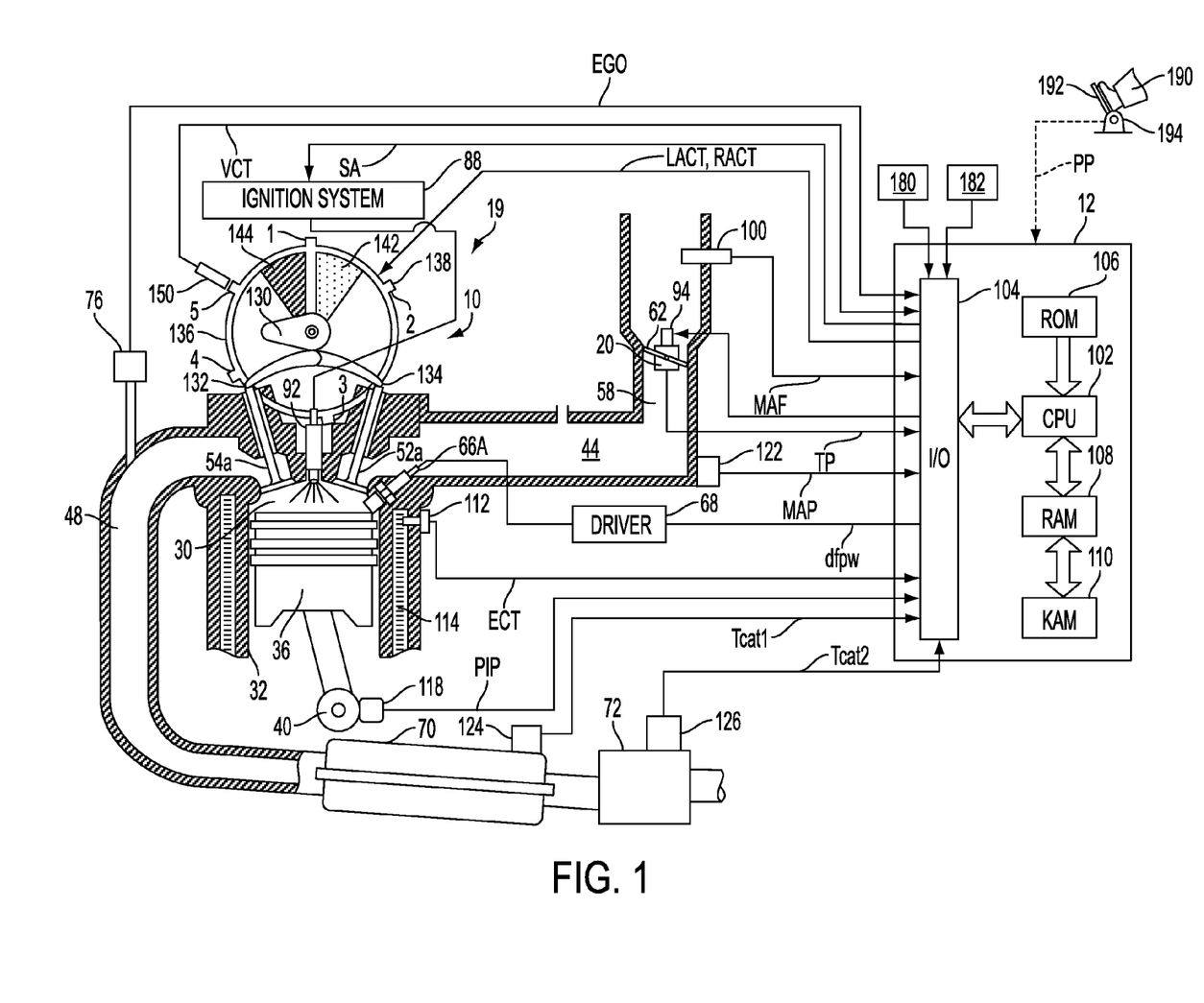
FIG. 1 shows a schematic diagram of a vehicle engine and related systems.

FIG. 1 depicts an example embodiment of a combustion chamber or cylinder of internal combustion engine 10. FIG. 1 shows that engine 10 may receive control parameters from a control system including controller 12, as well as input from a vehicle operator 190 via an input device 192. In this example, input device 192 includes an accelerator pedal and a pedal position sensor 194 for generating a proportional pedal position signal PP.

Cylinder (herein also "combustion chamber") 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of the passenger vehicle via a transmission system. Further, a starter motor may be coupled to crankshaft 40 via a flywheel to enable a starting operation of engine 10. Crankshaft 40 is coupled to oil pump 208 to pressurize the engine oil lubrication system 200 (the coupling of crankshaft 40 to oil pump 208 is not shown). Housing 136 is hydraulically coupled to crankshaft 40 via a timing chain or belt (not shown).

Cylinder 30 can receive intake air via intake manifold or air passages 44. Intake air passage 44 can communicate with other cylinders of engine 10 in addition to cylinder 30. In some embodiments, one or more of the intake passages may include a boosting device such as a turbocharger or a supercharger. A throttle system including a throttle plate 62 may be provided along an intake passage of the engine for varying the flow rate and/or pressure of intake air provided to the engine cylinders. In this particular example, throttle plate 62 is coupled to electric motor 94 so that the position of elliptical throttle plate 62 is controlled by controller 12 via electric motor 94. This configuration may be referred to as electronic throttle control (ETC), which can also be utilized during idle speed control.

Combustion chamber 30 is shown communicating with intake manifold 44 and exhaust manifold 48 via respective intake valves 52a and 52b (not shown), and exhaust valves 54a and 54b (not shown). Thus, while four valves per cylinder may be used, in another example, a single intake and single exhaust valve per cylinder may also be used. In still another example, two intake valves and one exhaust valve per cylinder may be used.

Exhaust manifold 48 can receive exhaust gases from other cylinders of engine 10 in addition to cylinder 30. Exhaust gas sensor 76 is shown coupled to exhaust manifold 48 upstream of catalytic converter 70 (where sensor 76 can correspond to various different sensors). For example, sensor 76 may be any of many known sensors for providing an indication of exhaust gas air/fuel ratio such as a linear oxygen sensor, a UEGO, a two-state oxygen sensor, an EGO, a HEGO, or an HC or CO sensor. Emission control device 72 is shown positioned downstream of catalytic converter 70. Emission control device 72 may be a three-way catalyst, a NOx trap, various other emission control devices or combinations thereof.

In some embodiments, each cylinder of engine 10 may include a spark plug 92 for initiating combustion. Ignition system 88 can provide an ignition spark to combustion chamber 30 via spark plug 92 in response to spark advance signal SA from controller 12, under select operating modes. However, in some embodiments, spark plug 92 may be omitted, such as where engine 10 may initiate combustion by auto-ignition or by injection of fuel, as may be the case with some diesel engines.

In some embodiments, each cylinder of engine 10 may be configured with one or more fuel injectors for providing fuel thereto. As a non-limiting example, fuel injector 66A is shown coupled directly to cylinder 30 for injecting fuel directly therein in proportion to the pulse width of signal dfpw received from controller 12 via electronic driver 68. In this manner, fuel injector 66A provides what is known as direct injection (hereafter also referred to as "DI") of fuel into cylinder 30.

Controller 12 is shown as a microcomputer, including microprocessor unit 102, input/output ports 104, an electronic storage medium for executable programs and calibration values shown as read only memory chip 106 in this particular example, random access memory 108, keep alive memory 110, and a conventional data bus. Controller 12 is shown receiving various signals from sensors coupled to engine 10, in addition to those signals previously discussed, including measurement of inducted mass air flow (MAF) from mass air flow sensor 100 coupled to throttle 20; engine coolant temperature (ECT) from temperature sensor 112 coupled to cooling sleeve 114; a profile ignition pickup signal (PIP) from Hall effect sensor 118 coupled to crankshaft 40; and throttle position TP from throttle position sensor 20; absolute Manifold Pressure Signal MAP from sensor 122; an indication of knock from knock sensor 182; and an indication of absolute or relative ambient humidity from sensor 180. Engine speed signal RPM is generated by controller 12 from signal PIP in a conventional manner and manifold pressure signal MAP from a manifold pressure sensor provides an indication of vacuum, or pressure, in the intake manifold. During stoichiometric operation, this sensor can give an indication of engine load. Further, this sensor, along with engine speed, can provide an estimate of charge (including air) inducted into the cylinder. In one example, sensor 118, which is also used as an engine speed sensor, produces a predetermined number of equally spaced pulses every revolution of the crankshaft.

In this particular example, temperature $T_{cat1}$ of catalytic converter 70 is provided by temperature sensor 124 and temperature $T_{cat2}$ of emission control device 72 is provided by temperature sensor 126. In an alternate embodiment, temperature Tcat1 and temperature Tcat2 may be inferred from engine operation.

Continuing with FIG. 1, a variable camshaft timing (VCT) system 19 is shown. In this example, an overhead cam system is illustrated, although other approaches may be used Specifically, camshaft 130 of engine 10 is shown communicating with rocker arms 132 and 134 for actuating intake valves 52a, 52b and exhaust valves 54a, 54b. VCT system 19 may be oil-pressure actuated (OPA), cam-torque actuated (CTA), or a combination thereof. By adjusting a plurality of hydraulic valves to thereby direct a hydraulic fluid, such as engine oil, into the cavity (such as an advance chamber or a retard chamber) of a camshaft phaser, valve timing may be changed, that is advanced or retarded. As further elaborated herein, the operation of the hydraulic control valves may be controlled by respective control solenoids. Specifically, an engine controller may transmit a signal to the solenoids to move a valve spool that regulates the flow of oil through the phaser cavity. In one example, the solenoid may be an electrically actuated solenoid. As used herein, advance and retard of cam timing refer to relative cam timings, in that a fully advanced position may still provide a retarded intake valve opening with regard to top dead center, as just an example.

Camshaft 130 is hydraulically coupled to housing 136. Housing 136 forms a toothed wheel having a plurality of teeth 138. Housing 136 is mechanically coupled to crankshaft 40 via a timing chain or belt (not shown). Therefore, housing 136 and camshaft 130 rotate at a speed substantially equivalent to the crankshaft. However, by manipulation of the hydraulic coupling as described herein, the relative position of camshaft 130 to crankshaft 40 can be varied by hydraulic pressures in retard chamber 142 and advance chamber 144. By allowing high pressure hydraulic fluid to enter retard chamber 142, the relative relationship between camshaft 130 and crankshaft 40 is retarded. Thus, intake valves 52a, 52b and exhaust valves 54a, 54b open and close at a time earlier than normal relative to crankshaft 40. Similarly, by allowing high pressure hydraulic fluid to enter advance chamber 144, the relative relationship between camshaft 130 and crankshaft 40 is advanced. Thus, intake valves 52a, 52b, and exhaust valves 54a, 54b open and close at a time later than normal relative to crankshaft 40.

While this example shows a system in which the intake and exhaust valve timing are controlled concurrently, variable intake cam timing, variable exhaust cam timing, dual independent variable cam timing, dual equal variable cam timing, or other variable cam timing may be used. Further, variable valve lift may also be used. Further, camshaft profile switching may be used to provide different cam profiles under different operating conditions. Further still, the valvetrain may be roller finger follower, direct acting mechanical bucket, electrohydraulic, or other alternatives to rocker arms.

Continuing with the variable cam timing system, teeth 138, being coupled to housing 136 and camshaft 130, allow for measurement of relative cam position via cam timing sensor 150 providing signal VCT to controller 12. Teeth 1, 2, 3, and 4 may be used for measurement of cam timing and are equally spaced (for example, in a V-8 dual bank engine, spaced 90 degrees apart from one another) while tooth 5 may be used for cylinder identification. In addition, controller 12 sends control signals (LACT, RACT) to conventional solenoid valves (not shown) to control the flow of hydraulic fluid either into retard chamber 142, advance chamber 144, or neither.

Relative cam timing can be measured in a variety of ways. In general terms, the time, or rotation angle, between the rising edge of the PIP signal and receiving a signal from one of the plurality of teeth 138 on housing 136 gives a measure of the relative cam timing. For the particular example of a V-8 engine, with two cylinder banks and a five-toothed wheel, a measure of cam timing for a particular bank is received four times per revolution, with the extra signal used for cylinder identification.

As described above, FIG. 1 merely shows one cylinder of a multi-cylinder engine, and that each cylinder has its own set of intake/exhaust valves, fuel injectors, spark plugs, etc.

Figure 2:
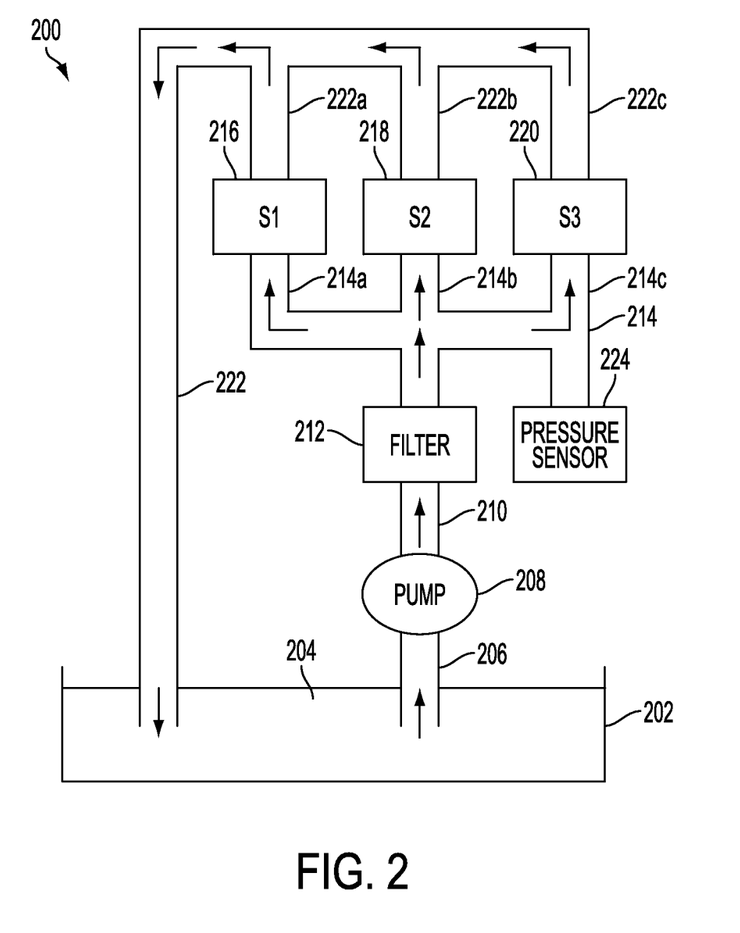
FIG. 2 shows a block diagram of an engine oil lubrication system.

FIG. 2 shows an example embodiment of an engine oil lubrication system 200 with an oil pump 208 coupled to crankshaft 40 (not shown), and including various oil subsystems 216, 218, 220. The oil subsystem may utilize oil flow to perform some function, such as lubrication, actuation of an actuator, etc. For example, one or more of the oil subsystems 216, 218, 220 may be hydraulic systems with hydraulic actuators and hydraulic control valves. Further, the oil subsystems 216, 218, 220 may be lubrication systems, such as passageways for delivering oil to moving components, such as the camshafts, cylinder valves, etc. Still further non-limiting examples of oil subsystems are camshaft phasers, cylinder walls, miscellaneous bearings, etc.

Oil is supplied to the oil subsystem through a supply channel and oil is returned through a return channel. In some embodiments, there may be fewer or more oil subsystems.

Continuing with FIG. 2, the oil pump 208, in association with the rotation of crankshaft 40 (not shown), sucks oil from oil reservoir 204, stored in oil pan 202, through supply channel 206. Oil is delivered from oil pump 208 with pressure through supply channel 210 and oil filter 212 to main galley 214. The pressure within the main galley 214 is a function of the force produced by oil pump 208 and the flow of oil entering each oil subsystem 216, 218, 220 through supply channels 214a, 214b, 214c, respectively. Oil returns to oil reservoir 204 at atmospheric pressure through return channel 222. Oil pressure sensor 224 measures main galley oil pressure and sends the pressure data to controller 12 (not shown).

The level of the main galley oil pressure can affect the performance of one or more of the oil subsystems 216, 218, 220, for example the force generated by a hydraulic actuator is directly proportional to the oil pressure in the main galley. When oil pressure is high, the actuator may be more responsive; when oil pressure is low, the actuator may be less responsive. Low oil pressure may also limit the effectiveness of engine oil to lubricate moving components. For example, if the main galley oil pressure is below a threshold pressure, a reduced flow of lubricating oil may be delivered, and component degradation may occur.

Additionally, the main galley oil pressure is highest when there is no or reduced flow of oil out of the main galley. Thus, leakage of hydraulic actuators in the oil subsystems can reduce main galley oil pressure. Further, one particular source of oil leakage can occur in the variable cam timing phaser, as described in further detail with regard to FIG. 3.

Figure 3:
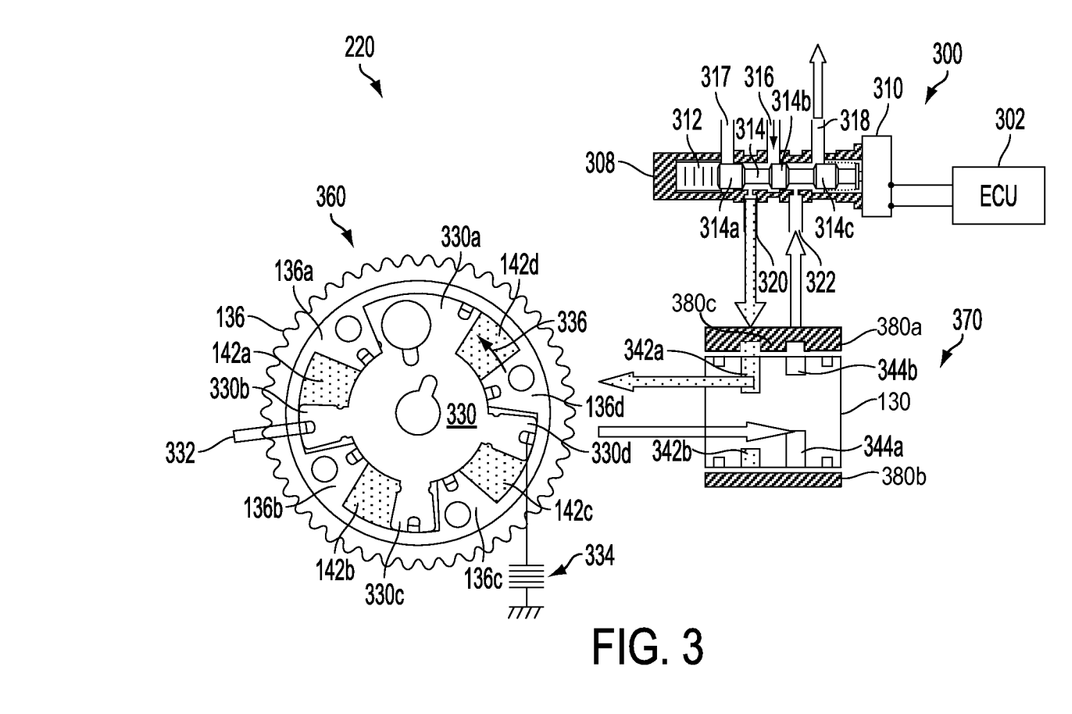
FIG. 3 shows an example VCT phaser and hydraulic system.

FIG. 3 shows an example oil subsystem 220. Oil subsystem 220 (herein also "phaser") is comprised of variable cam timing actuator (herein also "actuator") 360, variable force solenoid (herein also "solenoid") 310, oil control spool valve (herein also "spool valve") 300, cam journal 370, and hydraulic channels (herein also "channels") 316, 317, 318, 320, 322. Channel 316 connects main galley 214 to spool valve 300; channels 317, 318 connect spool valve 300 to return channel 222; channel 320 connects spool valve 300 to retard chamber 142 in actuator 360 via cam journal passage 342; channel 322 connects spool valve 300 to advance chamber 144 in actuator 360 via cam journal passage 344. Cam journal 370 includes camshaft 130, cam journal passages 342 and 344, cam journal cap 380, and cylinder head cam bore 381. Cam journal cap 380, mechanically coupled to the cylinder head (not shown), forms a cylindrical bearing within which camshaft 130 may rotate. In FIG. 3, a cut-away view of cam journal cap 380 is shown with cap top 380a, cylinder head cam bore 381, and cap seal landing 380c. Oil passages may be integrated into cam journal cap 380 as shown on either side of cap seal landing 380c. Cam journal passage 342 provides a hydraulic channel for oil between channel 320 and retard chamber 142. Cam journal passage 344 provides a hydraulic channel for oil between channel 322 and advance chamber 144. Cap seal landing 380c provides separation between cam journal passages 342 and 344. Thus, in one particular example, a cam-fed oil pressure actuated system may be used.

Actuator 360 is comprised of rotor 330, housing 136, retard chamber 142, advance chamber 144 (not shown), locking pin 332, and optional return spring 334. Rotor 330 is attached to camshaft 130 so it rotates at the same speed as camshaft 130. Rotor 330 is hydraulically coupled to housing 136. Phaser vanes 330a, 330b, 330c, 330d move within the recesses formed by retard chamber 142 and advance chamber 144. Spool valve 300 allows rotor 330 to move, by permitting oil flow into retard chamber 142 and out of advance chamber 144 or vice versa, depending on the desired direction of movement (that is, depending on whether a cam advance or a cam retard is desired). During a cam retard, oil from supply channel 316 flows through spool valve 300 and channel 320 and cam journal passage 342 into retard chamber 142 while oil is pushed from advance chamber 144 into cam journal passage 344 and channel 322 through spool valve 300 and out channel 318. During a cam advance, oil from supply channel 316 flows through spool valve 300 and channel 322 and cam journal passage 344 into advance chamber 144 while oil is pushed from retard chamber 142 into cam journal passage 342 and channel 320 through spool valve 300 and out channel 317. Housing 136 forms a mechanical stop for rotor 330. When retard chamber 142 is maximally open and rotor 330 is resting against housing 136, actuator 360 is at the retard end position (herein also "base position") and cam timing is maximally retarded. When advance chamber 144 is maximally open and rotor 330 is resting against housing 136, actuator 360 is at the advance end position and cam timing is maximally advanced. Optional return spring 334 and locking pin 332 may hold rotor 330 in the base position when oil pressure is low, such as during cold start. As oil pressure increases, locking pin 332 can be retracted so rotor 330 is free to move as described previously. When return spring 334 is present, return spring 334 generates a force that biases rotor 330 toward the base position regardless of oil pressure.

Spool valve 300 is comprised of a sleeve 308 for receiving a spool 314 with spool lands 314a, 314b, 314c and a biasing spring 312. Solenoid 310, controlled by electronic control unit (ECU) 302 (which may be controller 12), moves spool 314 within sleeve 308. The position of spool 314 is determined by balancing the force of biasing spring 312 against the force generated by solenoid 310. Spool landings 314a, 314b, 314c are used to restrict or block the flow of oil through the hydraulic channels. Spool 314 can be adjustable such that spool valve 300 operates among a plurality of ranges including a first range generating a hydraulic force in a first direction on the actuator toward a first end position, a second range generating a hydraulic force in a second, opposite direction on the actuator toward a second, opposite end, position, and a neutral range between the first and second ranges. In one example, the first range is a retard range, and the second range is an advancing range.

In the retarding range, oil flows from spool valve 300 into retard chamber 142 forcing actuator 360 to retard cam timing, up to the maximally retarded cam timing. Spool landing 314a blocks channel 317, a channel is open from channel 316 to channel 320 between spool landings 314a, 314b, and a channel is open from channel 322 to channel 318 between spool landings 314b, 314c. One case of the retarding range is when solenoid 310 is not energized (e.g. has no current applied to it) and actuator 360 is at the base position. In the advancing range, oil flows from spool valve 300 into advance chamber 144 forcing actuator 360 to overcome return spring 334 and advance cam timing, up to the maximally advanced cam timing. Spool landing 314c blocks channel 318, a channel is open from channel 316 to channel 322 between spool landings 314b, 314c, and a channel is open from channel 320 to channel 317 between spool landings 314a, 314b in the advancing range. In the neutral range, hydraulic forces on the actuator are substantially balanced so actuator 360 will neither advance nor retard cam timing. Torque from return spring 334 is countered by a positive pressure differential from advance chamber 144 to retard chamber 142. In the neutral range, spool landing 314c blocks channel 318, a weak channel is open from channel 316 to channel 322 between spool landings 314b, 314c, and a weak channel is open from channel 320 to channel 317 between spool landings 314a, 314b.

Figure 4:
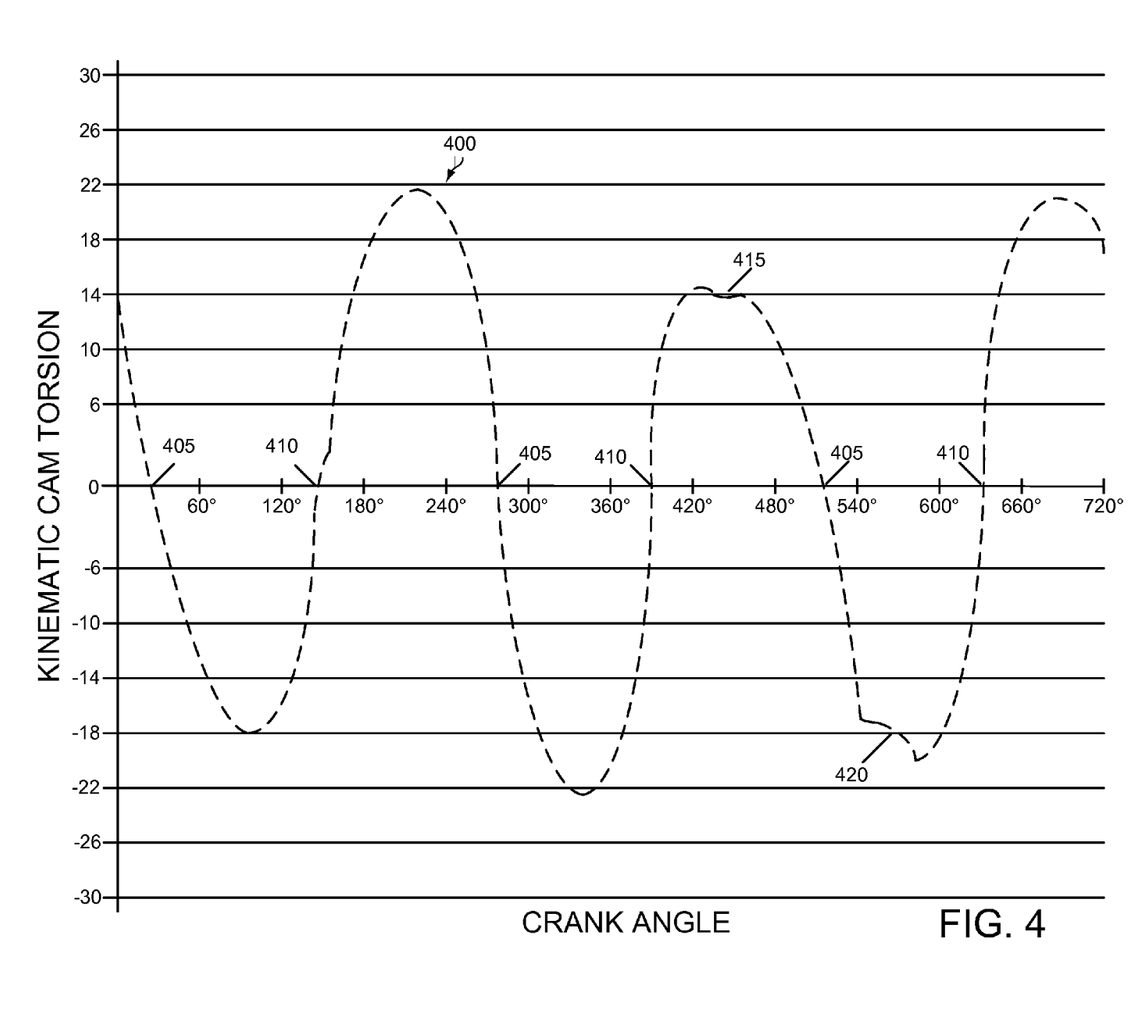
FIG. 4 depicts an example cam torque curve for a cam over a complete combustion cycle of a four-stroke cycle.

However, at certain engine conditions, the cam torsion may oscillate too fast for the spool valve to compensate solely through positional feedback. FIG. 4 depicts an example position curve 400 for an oscillating cam of the current disclosure and for a 3-cam V8 engine operating at 1000 RPM. FIG. 4 plots crank angle on the x-axis and kinematic cam torsion on the y-axis. Position curve 400 depicts a single cam passing through 720° of rotation at 1000 rpm. As shown in FIG. 4, over 720° of rotation there are 6 torque reversal events 405 and 410. Events 405 may correlate with a vane to stator transition where the VCT is transitioning to a retarding position. Events 410 may correlate with a pin to rotor transition, where the VCT is transitioning to an advancing position.

During these transition events, the cam position may be controlled with a spool valve as described above and shown in FIG. 3. However, the oscillating nature of the torque may occur faster than the control system is capable of compensating. When this oscillation occurs in a fashion that is opposed to the control oil entering the spool, oil may be forced out of the drain ports, moving the cam out of its desired position. This cam position error must be corrected for with additional oil entering the spool valve in subsequent control events. Examples of the cam position error are depicted at points 415 and 420 in position curve 400. As the cam torque oscillates, pressure may be generated in the drain port due to the incompressible nature of the oil, further contributing to cam position error. The inventors herein have determined that additional feedforward modulation may be utilized in order to counteract the loss of oil through the drain ports, thus yielding better cam position control.

Figure 5A:
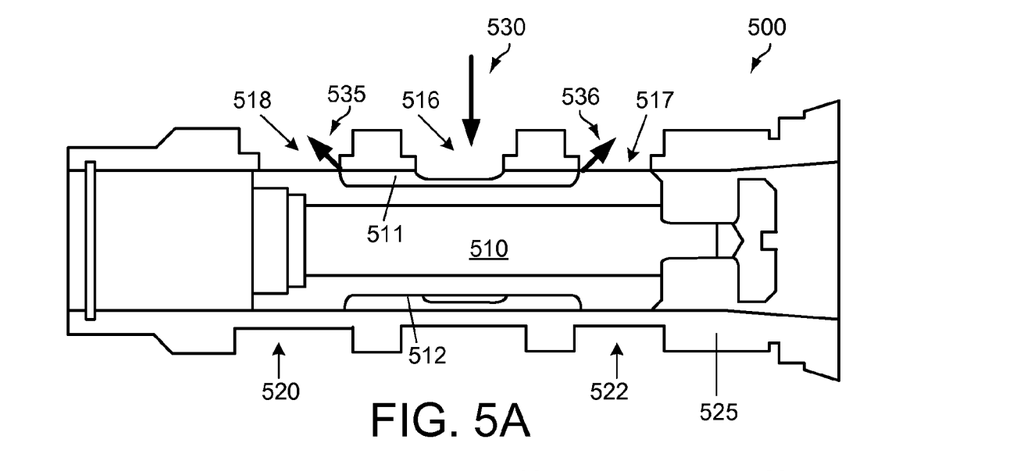
FIG. 5A shows a schematic diagram of a spool valve in a first position.
Figure 5B:
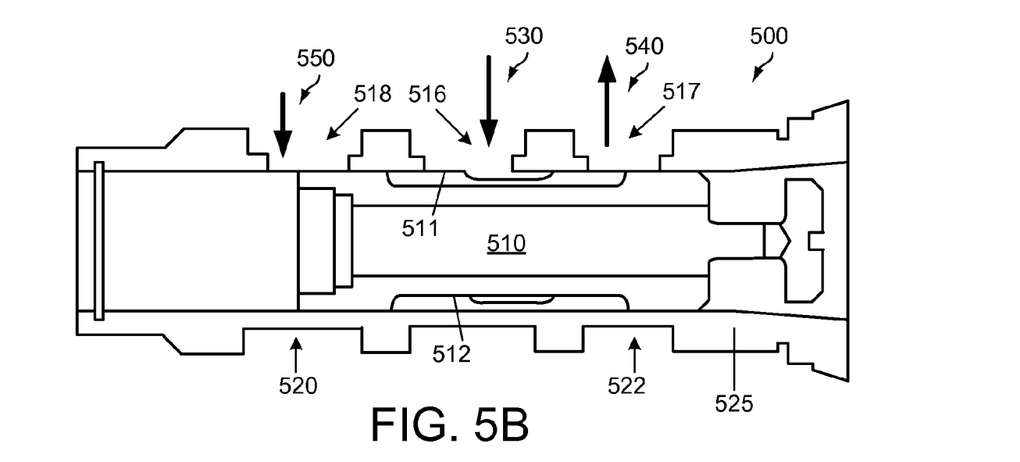
FIG. 5B shows a schematic diagram of a spool valve in a second position.
Figure 5C:
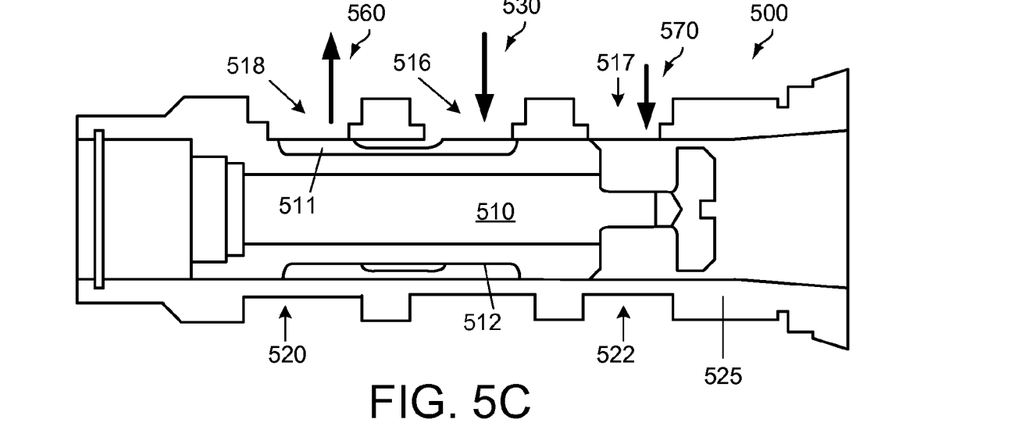
FIG. 5C shows a schematic diagram of a spool valve in a third position.

The feedforward modulation may be used to maintain a spool valve in a null position, and thereby blocking the drain ports, despite high frequency cam oscillation events. FIGS. 5A, 5B and 5C show schematic diagrams of a spool valve assembly 500 in a first, second and third position, respectively, and in accordance with the current disclosure. Spool valve 510 may be extended into or retracted from solenoid body 525 under the control of signals from a controller (not shown). Controller signals may actuate a hydraulic system or electrical system or other suitable system for moving spool valve 510. Spool valve 510 may include channels 511 and 512 which may change position in accordance with movement of spool valve 510 and may alter the characteristics of oil flow through assembly 500. Solenoid body 525 may be coupled to an inlet port 516 through which oil enters the assembly. Solenoid body 525 may also be coupled to an advance port 517 which may allow for oil to flow to the advance chamber of a VCT phaser vane. Solenoid body 525 may also include a retard port 518 which may allow for oil to flow to the retard chamber of a VCT phaser vane. Solenoid body 525 may also be coupled to drain ports 520 and 522 which may allow for oil to drain to an oil pan or other oil sump.

In FIG. 5A, spool valve assembly 500 is shown in a first position, herein also referred to as the "null" position. In the null position, spool valve 510 and channel 511 are in a position where the drain ports 520 and 525 are blocked. Oil may enter solenoid body 525 through inlet port 516, as depicted by arrow 530. Oil may trickle into advance port 517 and retard port 518 as depicted by arrows 536 and 535, respectively. In the null position, the oil entering the advance and retard ports may compensate for oil lost to leakage from these ports and the advance and retard chambers of the VCT phaser vane.

In FIG. 5B, spool valve assembly 500 is shown in a second position, herein also referred to as the "advance" position. In the advance position, spool valve 510 and channel 511 are in a position where oil may enter solenoid body 525 through inlet port 516, as depicted by arrow 530. Oil entering solenoid body 525 is forced through channel 511 and into advance port 517 as depicted by arrow 540. Oil may also drain out of retard port 518 as depicted by arrow 550, and may further exit solenoid body 525 through drain port 520. Thus, in the advance position, there may be a net flow of oil into the advance chamber of the VCT phaser vane and out of the retard chamber of the VCT phaser vane.

In FIG. 5C, spool valve assembly 500 is shown in a third position, herein also referred to as the "retard" position. In the retard position, spool valve 510 and channel 511 are in a position where oil may enter solenoid body 525 through inlet port 516, as depicted by arrow 530. Oil entering solenoid body 525 is forced through channel 511 and into retard port 518 as depicted by arrow 560. Oil may also drain out of advance port 517 as depicted by arrow 570, and may further exit solenoid body 525 through drain port 522. Thus, in the retard position, there may be a net flow of oil into the retard chamber of the VCT phaser vane and out of the advance chamber of the VCT phaser vane.

When in the null position, the spool valve depicted in FIG. 5 may allow for a drain to be blocked when the cam torque oscillation would normally force oil into the drain. The spool valve may also be positioned to block only one of the advance or retard drain ports. By controlling the position of the valve in unison with the cam torque oscillation, oil may be kept in the system that would otherwise be lost due to pressure generated from the cam torque.

Figure 6:
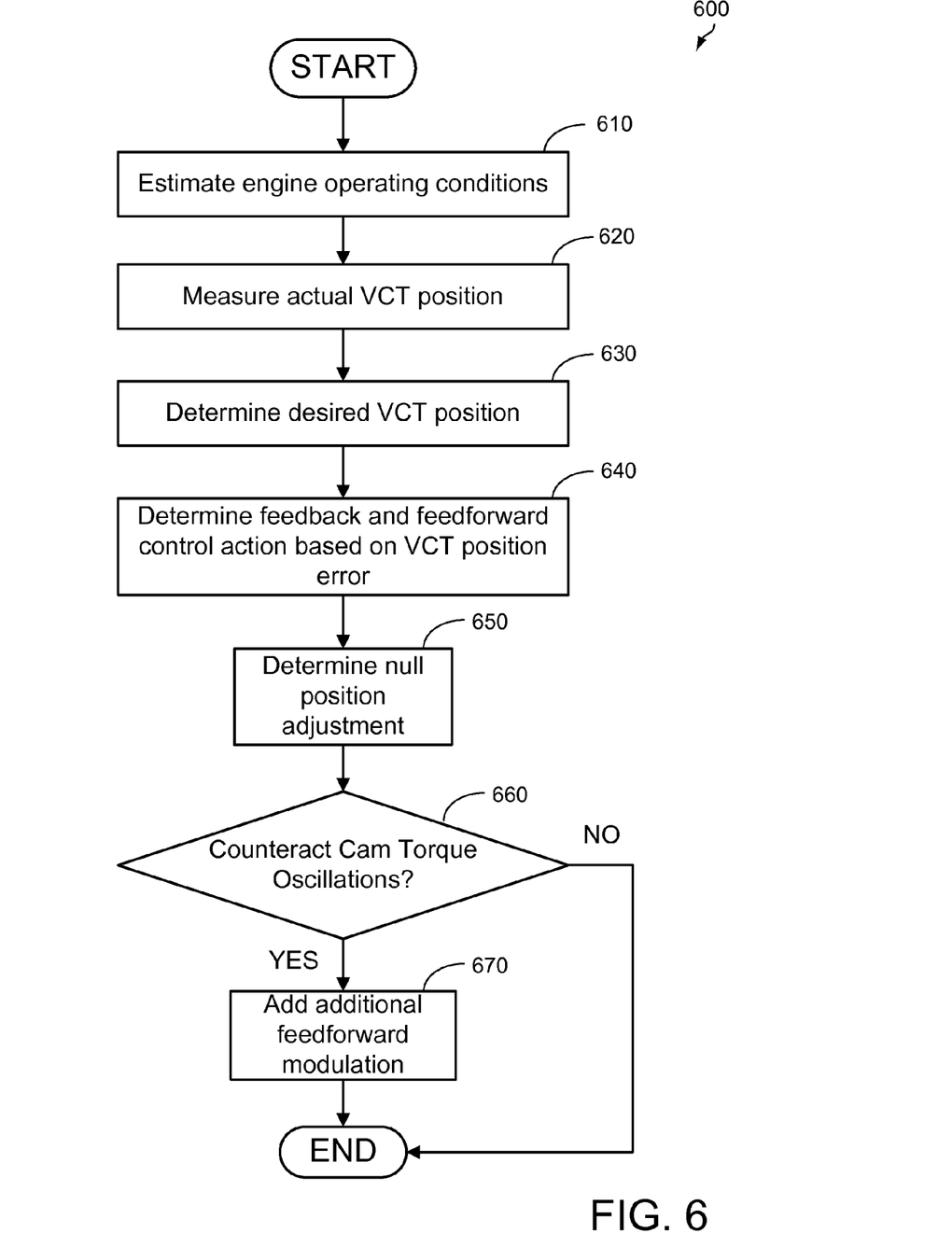
FIG. 6 shows an example high-level method for controlling spool valve positioning in accordance with the present disclosure.

FIG. 6 shows an example method 600 of controlling the position of the spool valve depicted in FIG. 5 in unison with the cam torque oscillation in accordance with the present disclosure. Method 600 may begin at 610. At 610, current engine operating conditions may be estimated or measured. Conditions assessed may include barometric pressure, driver-demanded torque, manifold pressure, manifold air flow, engine temperature, air temperature, knock limits and other operating conditions. Next, at 620, the current position of the VCT may be measured. This may include determining the cam angle, cam torsion, cam phase, and other conditions of the VCT system. At 630, the desired position of the VCT may be determined based on the engine operation conditions. In one example, actuating the spool valve to advance and retard the hydraulic variable cam timing actuator is in response to an error between a desired cam timing a current cam timing.

At 640, the controller may determine feedback and feedforward control actions based on the VCT position error between the actual VCT position and the desired VCT position. For example, if the VCT is in a retarding position when engine conditions suggest the VCT should be in an advancing position, a feedback control action may dictate the spool valve should be actuated to move from a current position to an advancing position (for example, the position depicted in FIG. 5B), allowing oil to enter the advancing vane of the VCT phaser. Additionally, feedforward constants and control actions may be determined at 640 that may be used at 650 and 670 of method 600 as further described below.

At 650, the controller may determine the null position adjustment based on the engine operating conditions, actual and desired VCT positions, and feedback and feedforward constants and control actions. This may include setting a value of a null duty cycle based on the operating conditions. In some cases, the null duty cycle may be equal to 0.5 in order to set the position of the spool valve in the null position, thus blocking the drain ports in the solenoid assembly. However, the engine conditions may require setting the duty cycle at a higher or lower value (for example 0.51 or 0.45) in order to set the position of the spool valve in the null position. The null position duty cycle may be dependent on the cylinder mode of operation or other engine operating conditions.

At 660, the controller may determine whether cam torque oscillations need to be counteracted based on the engine operating conditions, the actual and desired VCT positions, and the feedback and feedforward constants and control actions. In one example, at a threshold engine RPM, the cam torque oscillations may be occur too rapidly to be effectively controlled solely through feedback. In one example, modulating in the null position may only be carried out at engine speeds above an upper threshold speed. The duty cycle actuating the solenoid to position the spool valve in the null position may require additional modulation in order to counteract the kinematic cam torsion. If the controller determines that no additional modulation is required to counteract the cam torque oscillations, method 600 may end. If the controller determines that additional modulation is required to counteract the cam torque oscillations, method 600 may proceed to 670. At 670, additional modulation may be added. The modulation may be a feedforward control action.

For example, if the duty cycle is set at 0.5, the additional modulation may include cycling the duty cycle +/−0.02 at a frequency synchronous to the engine firing frequency. The amplitude of the modulation may be adjusted based on engine speed, current cam timing, desired cam timing, etc. In the example depicted in FIG. 4, the engine is a V8 engine operating at 1000 RPM, where 6 oscillation events occur per 16 firing events. As such, the solenoid may be modulated such that the modulation frequency is set at a dominant component at a frequency of ⅜ of the engine firing frequency in order to counteract kinematic cam torsion. In another example, a V6 engine may be operating at 1000 RPM, where 6 oscillation events occur per 12 firing events. In this example, the modulation frequency may be set at ½ of the firing frequency of the engine in order to counteract kinematic cam torsion. In other examples, the modulation frequency may be set equal to engine firing frequency, or at a value equal to twice the engine firing frequency, or at any value that synchronizes cam oscillation with solenoid actuation such that the drain ports of the solenoid assembly are blocked through a feedforward mechanism that counteracts the kinematic cam torsion. The component at the synchronous frequency may include an additional component at 1/N of firing frequency, where N is the number of cylinders in the engine. In another example, the modulating may be out of phase with engine firing by a selected amount. Once additional feedforward modulation has been added to the solenoid control signal, method 600 may end.

Figure 7:
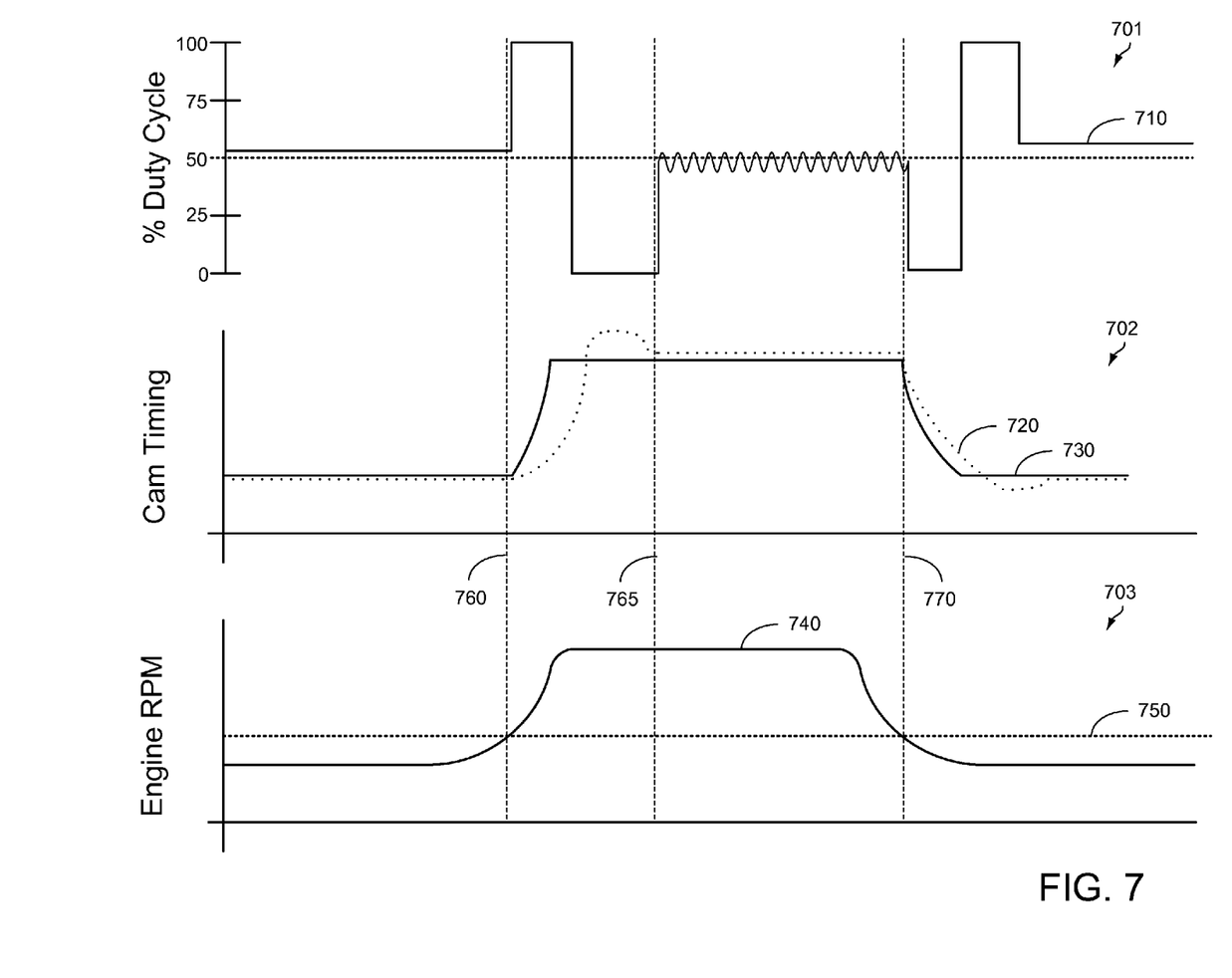
FIG. 7 depicts prophetic example data illustrating the control of spool valve positioning for example engine conditions in accordance with the present disclosure.

FIG. 7 depicts a prophetic example set of engine conditions, VCT positioning, and a solenoid activation signal that may be applied as an actuation of method 600 or other such methods in accordance with the current disclosure. Plots 701, 702 and 703 are depicted as being to the same scale of time in seconds on the x-axis.

Plot 701 depicts a solenoid activation signal as a percentage of duty cycle over a period of time in accordance with the current disclosure. The duty cycle may take any value between 0 and 100%. At 0% duty cycle, the solenoid is activated to control the spool valve in the full retarding position, e.g. the position shown in FIG. 5C. At 100% duty cycle, the solenoid is activated to control the spool valve in the full advancing position, e.g. the position shown in FIG. 5B. In the absence of other factors, at 50% duty cycle, the solenoid may be activated to control the spool valve in the null position, e.g. the position shown in FIG. 5A. Line 710 depicts an example. However, as described above, engine operating conditions may necessitate the duty cycle be greater than or less than 50% in order to maintain the spool valve in the null position.

Plot 702 depicts a plot of cam timing over time in accordance with the present disclosure. Line 730 depicts desired cam timing, whereas line 740 depicts actual cam timing. In this plot, values above the intercept are indicative of VCT advancing. Values below the intercept, (none depicted) are indicative of VCT retarding.

Plot 703 depicts a plot of engine RPM over time. Line 740 depicts engine RPM. Line 750 depicts a threshold RPM value, above which cam torque oscillations may require additional feed forward modulation, as depicted and discussed with regard to FIG. 6.

In this example, initially, engine RPM 740 is below threshold 750 and desired cam timing 730 is within the margin of error of the actual cam timing. The solenoid activation signal is held at approximately 51% duty cycle to maintain the spool valve in the null position.

As depicted, plot 703 shows engine RPM increasing above threshold 750 at time 760. Desired cam timing, as depicted by line 730 may increase towards fully advancing in accordance with the increase in engine RPM among other engine operating conditions (not shown). Thus, at time 760 when the engine RPM increases above threshold 750, the controller may increase the solenoid activation signal towards 100% duty cycle, thereby moving the spool valve to an advancing position.

As shown by line 720 in plot 702, increasing the solenoid activation signal in the manner depicted may cause the actual cam timing to increase above the desired cam timing 730. In this example, the solenoid activation signal may decrease towards fully retarding as determined through feedback.

At 765, when the desired cam timing 730 is within the margin of error of the actual cam timing 720, the solenoid activation signal may adjusted by the controller to maintain the null position by increasing the duty cycle to 49%. However, since engine RPM 740 is maintained above threshold 750, additional feedforward modulation may be needed to maintain the spool valve in the null position. In this example, modulation is added at +/−2% of duty cycle at ⅜ firing frequency.

As depicted for this example, the feedforward modulation is maintained until engine RPM 740 drops below threshold 750 at time 770. As the desired cam timing decreases, the controller may decrease the solenoid activation signal towards 0% duty cycle, thereby moving the spool valve to a retarding position.

As shown by line 720 in plot 702, decreasing the solenoid activation signal in the manner depicted may cause the actual cam timing to decrease below the desired cam timing 730. In this example, the solenoid activation signal may increase towards fully advancing as determined through feedback. When the desired cam timing 730 is within the margin of error of the actual cam timing 720, the solenoid activation signal may adjusted by the controller to maintain the null position by increasing the duty cycle to 55%. As engine RPM 740 is maintained below threshold 750, additional feedforward modulation may not be needed to control the spool valve in the null position.

In this way, it is possible to generate actuation of the spool valve to counteract the effects of the cam torque on the oil flow, so that the oil volume in the variable cam timing actuator is maintained and the cams better maintain the current cam timing.

It will be appreciated that the configurations and routines herein are exemplary in nature, and that these specific embodiments are not to be considered in a limiting sense, because numerous variations are possible. For example, the above technology can be applied to V-6, I-4, I-6, V-12, opposed 4, gasoline, diesel and other engine types and fuel types. The subject matter of the present disclosure includes all novel and nonobvious combinations and subcombinations of the various systems and configurations, and other features, functions, and/or properties discussed herein.

The following claims particularly point out certain combinations and subcombinations regarded as novel and nonobvious. The claims may refer to "an" element or "a first" element or the equivalent thereof. Such claims should be understood to include incorporation of one or more such elements, neither requiring nor excluding two or more such elements. Other combinations and sub-combinations of features, functions, elements, and/or properties may be claimed through amendments of the present claims or through presentation of new claims in this or a related application. Such claims, whether broader, narrower or equal, or different in scope to the original claims, also are regarded as included within the subject matter of the present disclosure.

The invention claimed is:

1. A method, comprising:
actuating a spool valve via a solenoid to advance and retard a hydraulic variable cam timing actuator coupled to a camshaft; and
while commanded to a null position to maintain current cam timing, modulating the solenoid with a component at a frequency synchronous to engine firing frequency, aligning the modulating to a kinematic torsion acting on the camshaft to counteract cam torque oscillations.

2. The method of claim 1, wherein the solenoid is modulated with a dominant component at a frequency of ⅜ engine firing frequency.

3. The method of claim 1, wherein the solenoid is an electrically actuated solenoid.

4. The method of claim 1, wherein the modulation is a feedforward control action.

5. The method of claim 1, wherein an amplitude of the modulation is further adjusted based on engine speed and current cam timing.

6. The method of claim 1, wherein actuating the spool valve to advance and retard the hydraulic variable cam timing actuator is in response to an error between a desired cam timing and current cam timing.

7. The method of claim 1, wherein the component at the synchronous frequency includes an additional component at 1/N of firing frequency, where N is a number of cylinders in the engine.

8. The method of claim 1, wherein the modulating in the null position is only carried out at engine speeds above an upper threshold speed.

9. The method of claim 1, wherein the modulating is out of phase with engine firing by a selected amount.

10. A system for an engine, comprising:
a hydraulically actuated variable cam timing actuator;
a cam with oil passages used to deliver oil from oil passages in a cam cap to the variable cam timing actuator coupled to the cam;
a hydraulic spool valve coupled to the variable cam timing actuator, the spool valve adjustable among a plurality of positions including a null position to maintain current cam timing; and
a solenoid configured to control the position of the spool valve by modulating the spool valve in the null position with a component at a frequency synchronous to engine firing frequency, aligning the modulating to a kinematic torsion acting on the camshaft to counteract cam torque oscillations.

11. The system of claim 10, wherein the solenoid is an electrically actuated solenoid.

12. The system of claim 10, wherein the modulation is a feedforward control action.

13. The system of claim 10, wherein the modulating in the null position is only carried out at engine speeds above an upper threshold speed.

14. The system of claim 10, wherein an amplitude of the modulation is further adjusted based on engine speed and current cam timing.

15. The system of claim 10, wherein the component at the synchronous frequency includes an additional component at 1/N of firing frequency, where N is a number of cylinders in the engine.

16. A method, comprising:
actuating a spool valve via a solenoid to advance and retard a hydraulic variable cam timing actuator coupled to a camshaft; and only at engine speeds above an upper threshold speed, while commanded to a null position to maintain current cam timing, modulating the solenoid with a component at a frequency synchronous to engine firing frequency including at 1/N of firing frequency, N being a number of engine cylinders.

17. The system of claim 16, wherein the solenoid is an electrically actuated solenoid.

18. The system of claim 16, wherein the modulation is a feedforward control action.

19. The system of claim 16, wherein an amplitude of the modulation is further adjusted based on engine speed and current cam timing.

20. The method of claim 16, wherein the modulating is out of phase with engine firing by a selected amount.

* * * * *